United States Patent [19]
Seiler

[11] Patent Number: 6,038,706
[45] Date of Patent: *Mar. 21, 2000

[54] CONVERTIBLE PROTECTIVE COVER FOR A MASK

[76] Inventor: Douglas A. Seiler, 127 Iolanthus Ave., Novato, Calif. 94945

[*] Notice: This patent is subject to a terminal disclaimer.

[21] Appl. No.: 09/076,350

[22] Filed: May 12, 1998

Related U.S. Application Data

[63] Continuation-in-part of application No. 08/857,142, May 15, 1997, Pat. No. 5,878,443.
[51] Int. Cl.$^7$ .............................. A61F 9/02; A45C 11/04
[52] U.S. Cl. ........................................ 2/426; 2/452; 206/5
[58] Field of Search ............................ 206/5; 2/426, 434, 2/438, 452, 454; 224/255

[56] References Cited

U.S. PATENT DOCUMENTS

| | | |
|---|---|---|
| 4,910,806 | 3/1990 | Baker et al. . |
| 5,014,846 | 5/1991 | Walker et al. . |
| 5,102,216 | 4/1992 | Mitchell . |
| 5,151,778 | 9/1992 | Conley . |
| 5,299,682 | 4/1994 | Tater . |
| 5,344,002 | 9/1994 | Baczkowski . |
| 5,366,072 | 11/1994 | Goldenberg . |
| 5,593,024 | 1/1997 | Seiler . |
| 5,687,837 | 11/1997 | Seiler . |
| 5,735,393 | 4/1998 | Shiue et al. . |
| 5,878,443 | 3/1999 | Seiler . |
| 5,881,394 | 3/1999 | Garofalo . |
| 5,894,606 | 4/1999 | Chiang . |

*Primary Examiner*—John J. Calvert
*Assistant Examiner*—Shirra L. Jenkins
*Attorney, Agent, or Firm*—Foley & Lardner

[57] ABSTRACT

A case for a mask includes a first panel secured to a second panel to form a pouch into which the mask may be inserted and removed. The second panel may include a pair of overlapping panel sections defining an opening for insertion of the mask. Apertures on either side of the case accommodate passage of a strap attached to the mask. Alternatively, straps may be permanently secured to the case. Closure elements on either side of the opening maintain the case in a closed position. The case may be positioned behind the user's head when the mask is being used, cushioning the strap, and may be inverted into a storage configuration to cover at least the mask lens. The closure elements are oriented in mutually facing relation in both configurations to maintain the case closed. Panels of the case may be made of floatable synthetic materials or may include light-weight or net materials to promote drying of the case and mask following use. Various embodiments are disclosed for the substantially complete enclosing of a mask within a pouch, as well as an embodiment for the covering only of the outer surfaces of the primary lenses of a mask, those surfaces being the most vulnerable to scratching in unprotected storage, whereby the uncovered portions of the mask remain exposed to ambient air and may thereby dry more quickly. Also disclosed is a method of protecting a mask, such as are used in diving and/or skiing, from scratching of lenses and similar damage or degradation while in storage by at least partially enclosing the mask within a pouch, the pouch being formed by reconfiguring a cushion of the strap for the mask.

19 Claims, 12 Drawing Sheets

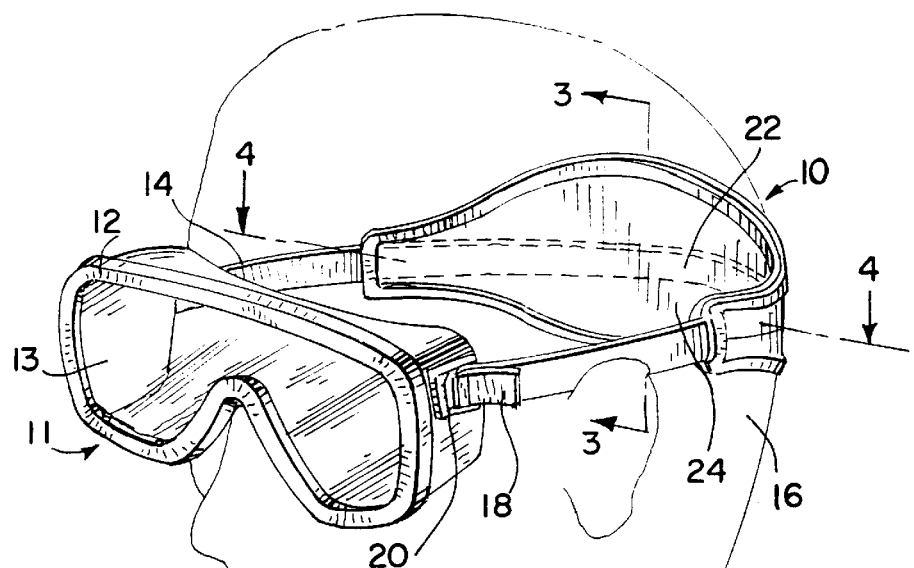
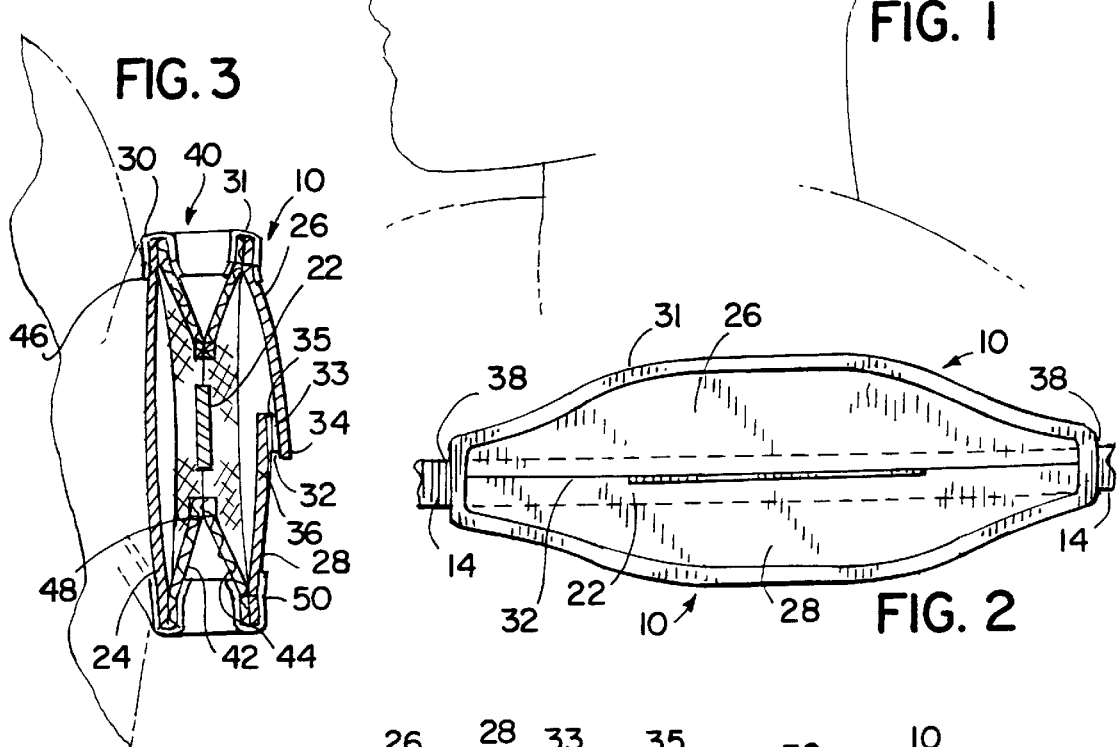
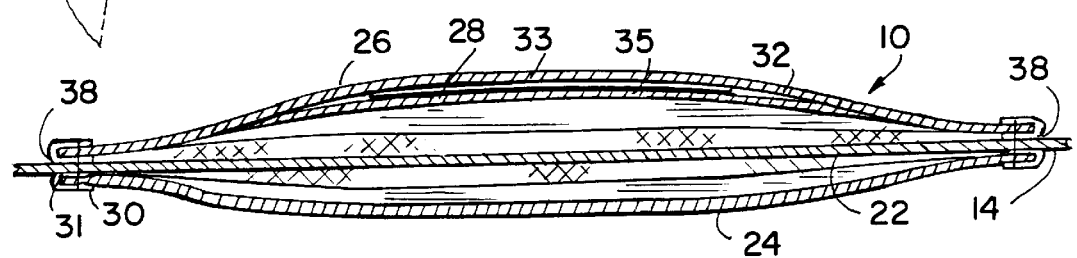

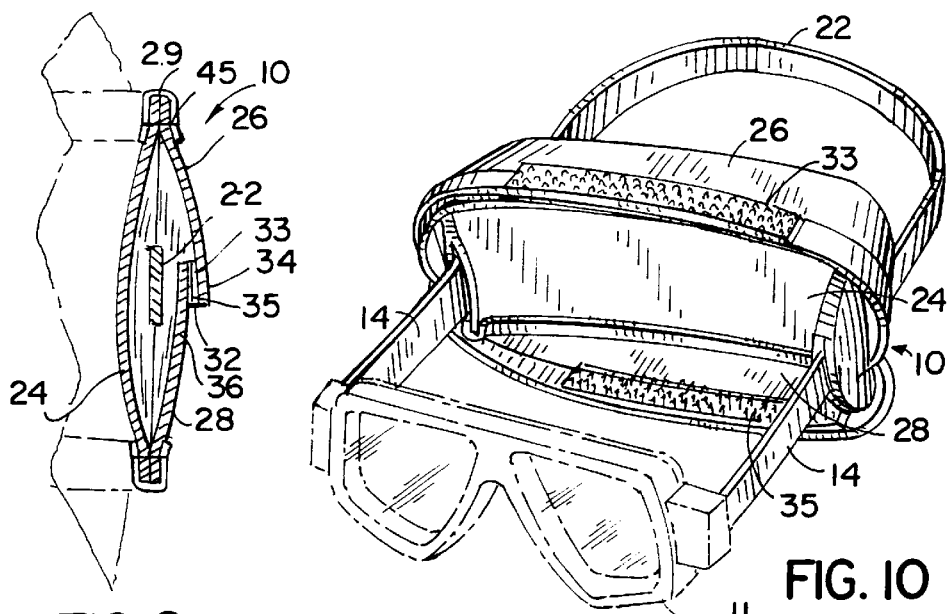
FIG. 9
FIG. 10
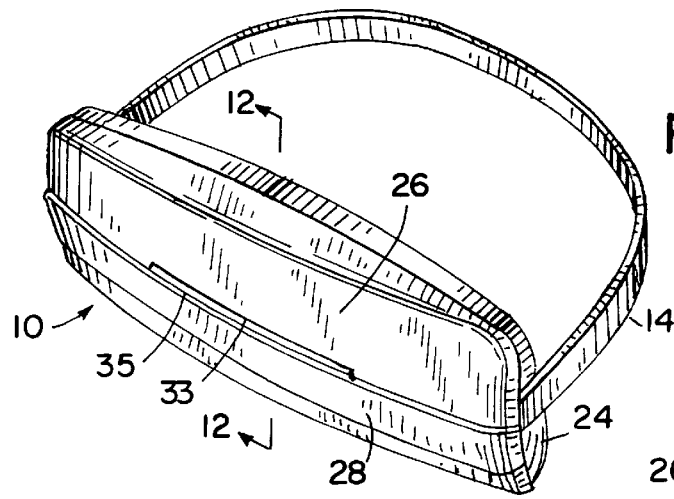
FIG. 11
FIG. 12
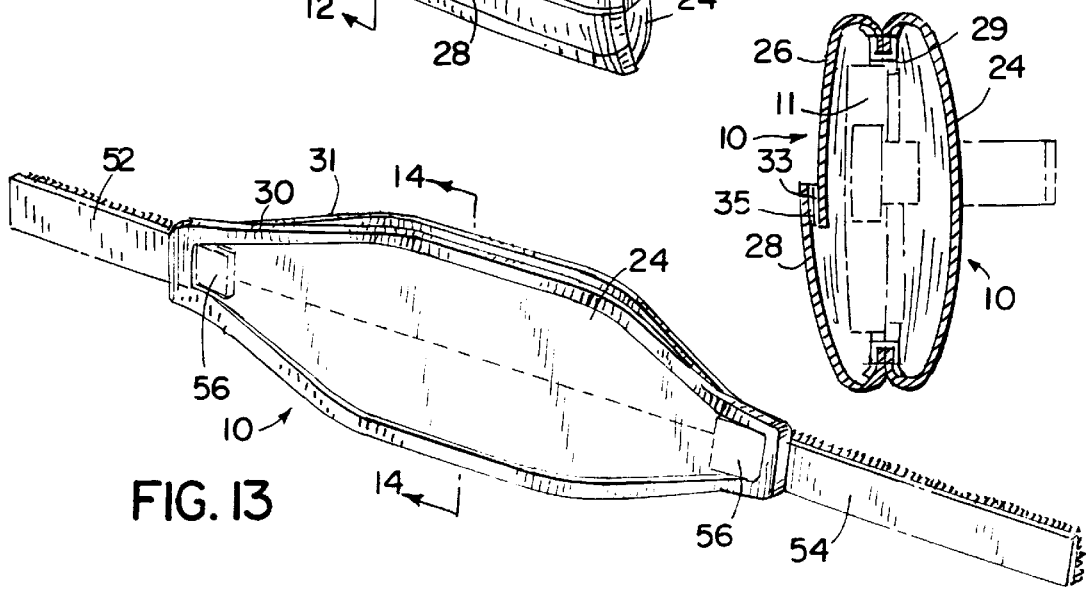
FIG. 13

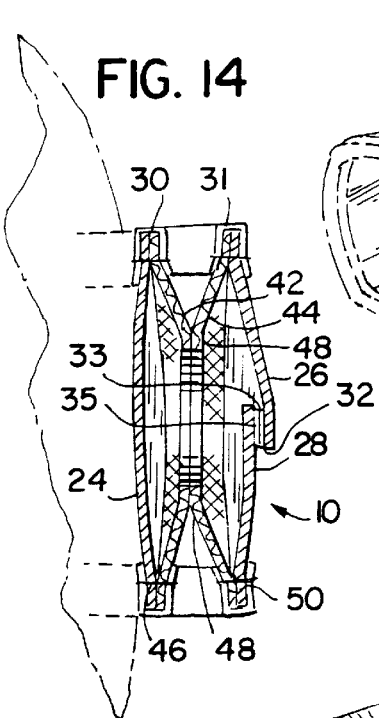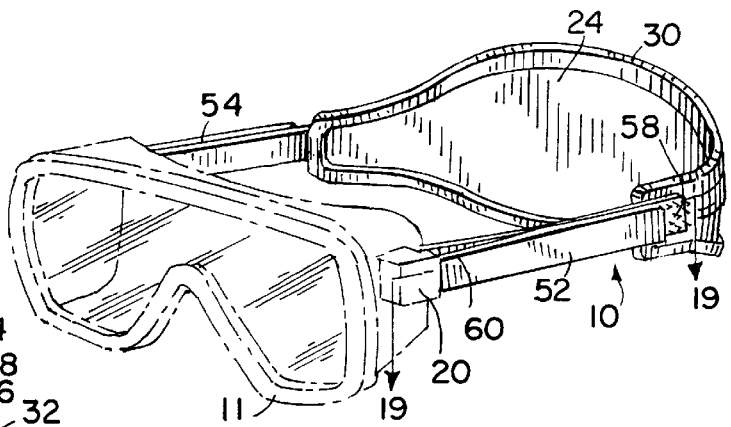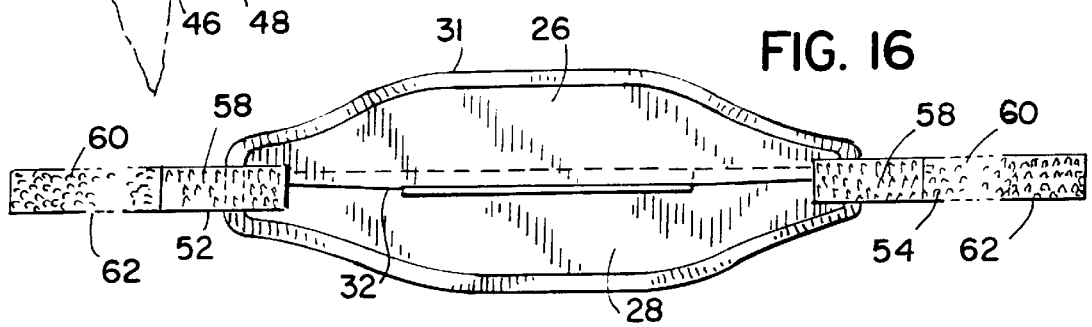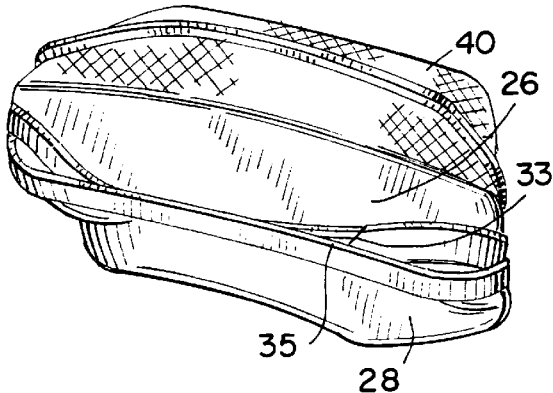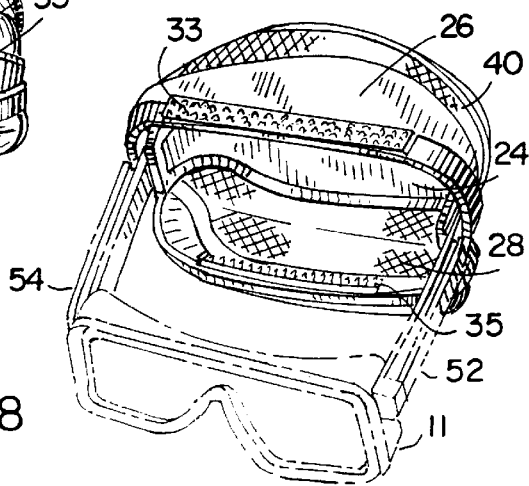
FIG. 14
FIG. 15
FIG. 16
FIG. 17
FIG. 18

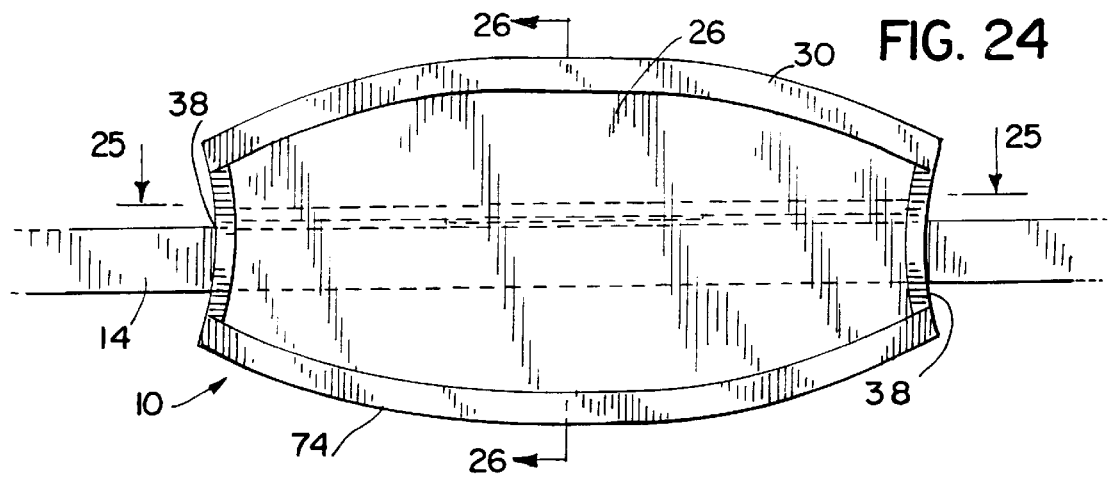
FIG. 24
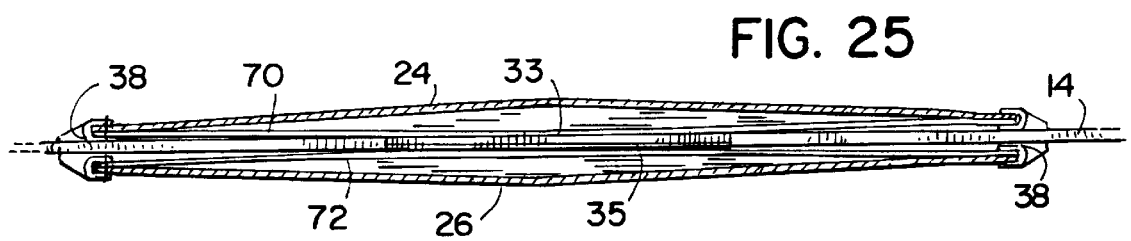
FIG. 25
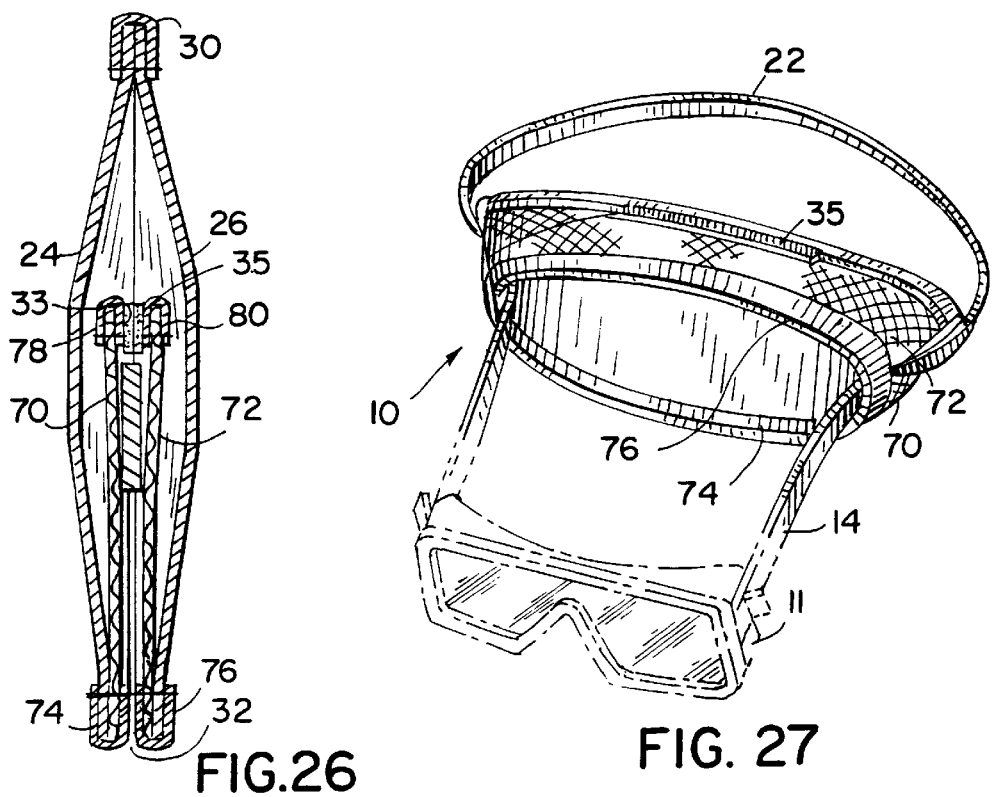
FIG. 26
FIG. 27

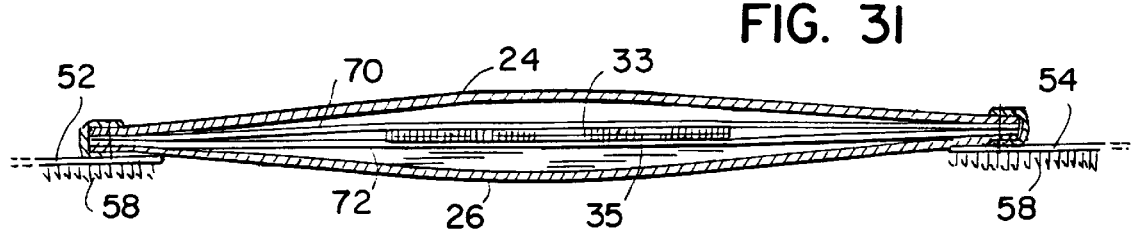
FIG. 31
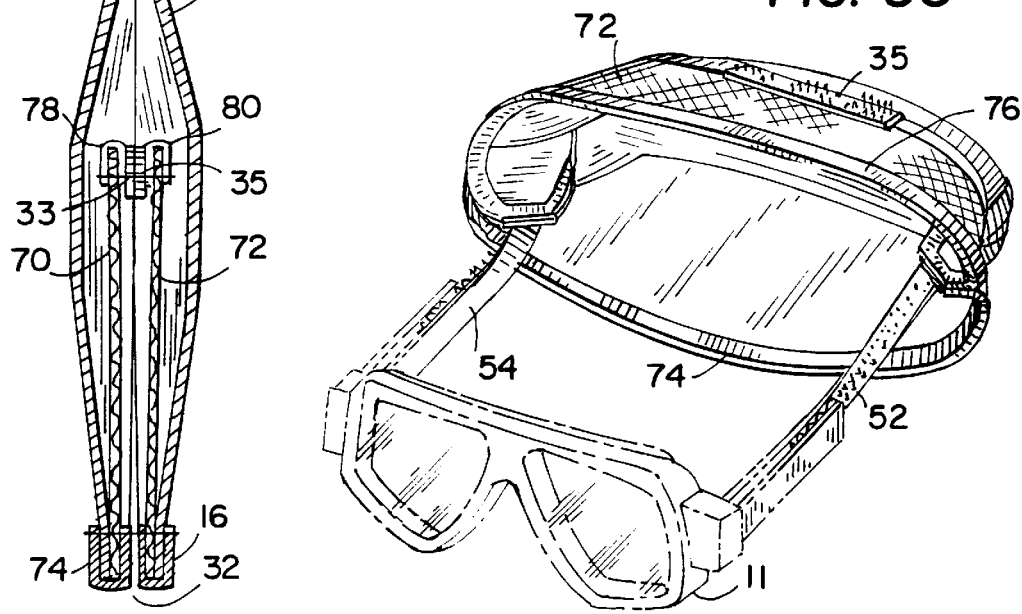
FIG. 32
FIG. 33
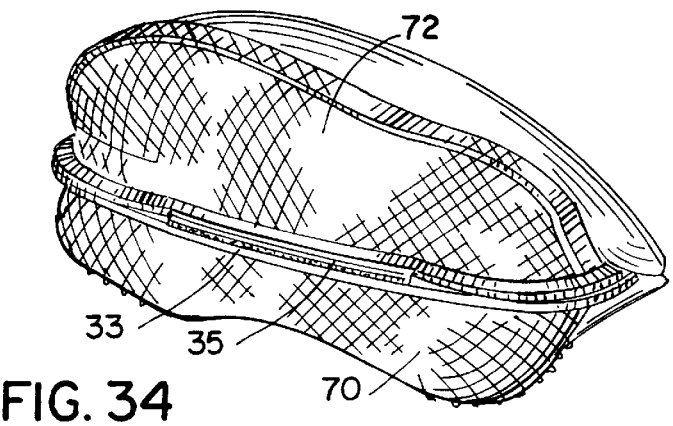
FIG. 34

CONVERTIBLE PROTECTIVE COVER FOR A MASK

This application is a continuation-in-part of application Ser. No. 08/857,142, now U.S. Pat. No. 5,878,443 issued Mar. 9, 1999.

FIELD OF THE INVENTION

The present invention relates generally to the field of protective cases or covers for masks, such as diving or ski masks. More particularly, the invention relates to a soft, flexible case for a mask that can be worn behind the user's head when the mask is in use and which may be used for storing the mask without detaching the mask from the case.

BACKGROUND OF THE INVENTION

Masks commonly used by underwater divers, snorkeling swimmers, downhill skiers and the like, typically include a front mask portion with a single or double viewing window or lens, and a strap designed to encircle the user's head to hold the mask tightly in place over the user's eyes. The mask portion is usually made of a flexible rubber composition that seals against the user's skin when in use to prevent water, snow or other materials from entering into the mask and obscuring the user's vision. Such masks may also fit over the user's nose as well. Attachment rings or similar structures on either side of the mask permit the strap to be firmly attached and adjusted to provide the desired level of sealing and comfort for the user. Increasingly, such masks include fairly sensitive viewing windows or lenses, sometimes including corrective optics, that can be easily scratched or otherwise damaged when the mask is not in use.

Despite the risk of damage to the mask viewing window, however, many divers, snorkelers and skiers care for such masks simply by rinsing or wiping them after use and storing them along with other equipment, such as in an equipment bag or the like. In such cases, the lenses of the masks may be inadvertently scratched, broken or otherwise damaged between uses. While special bags may be used for storing the mask individually, such bags are separable from the mask and must be located for storage of the mask following use. The mask remains, therefore, exposed to damage upon return to a dive boat, shore or lodge until the bag can be located and the mask inserted therein.

Another drawback with conventional sport masks is that the strap used to secure the mask to the user's head, typically an elastic rubber or similar flexible strip, may bind on the user's hair or otherwise cause discomfort to the user along the region where it contacts the back of the user's head. Various solutions have been proposed to isolate such straps from the user's hair and to provide a limited degree of padding between the strap and the user's head. In one known arrangement, an elastic panel is secured to a pair of ribbon members that are designed for attachment to the mask. In another known device, a removable elastic panel is designed to receive a portion of a mask strap and to remain attached to the strap both during use and storage. Such elastic panels provide a region over which pressure exerted by the strap may be distributed, reducing discomfort to the user. However, such panels do not provide for storage of the mask, and must generally be placed, along with the mask and strap, in an equipment bag or the like following use, again exposing the mask lenses to potential damage.

There is a need, therefore, for an improved case for sports masks capable of offering convenient storage of a mask when not in use, and which need not be detached from the mask when secured to the user's head. Moreover, there is a need for a mask case that provides padding or otherwise improves the comfort level for the user when wearing the mask, by distributing loads exerted by the securing strap behind the user's head then the mask is worn.

SUMMARY OF THE INVENTION

The present invention features a novel case designed to respond to these needs. The case provides a convenient storage bag or envelope for the mask when not in use and may remain attached to the mask strap, positioned comfortably behind the user's head when the mask is worn. The case may be formed with apertures for passing the strap therethrough, or may be permanently secured to the straps to form an attachment assembly fitted to the mask. In a preferred configuration, the case collapses to a relatively small, padded panel that provides padding for the mask strap, and is inverted over the mask as the mask is inserted therein following use. The case may be made of a variety of materials, including rubber or other synthetic compositions that provide added buoyancy to the mask, thereby preventing or inhibiting sinking of the mask if dropped into water.

Thus, in accordance with a first aspect of the invention, a case is provided for a mask of the type including a frame, a lens supported in the frame, and a strap attached to the frame and configured to partially encircle the head of a user to hold the frame against the user's face. The case includes flexible front and rear panels and first and second side apertures. The front panel is configured to bear against the user's head when worn. The rear panel is secured to the front panel along a border region to define a pouch having a central opening through which the mask may be inserted into and removed from the pouch. The side apertures are defined on either side of the central opening for receiving the strap for holding the case on a central region of the strap. The case is attachable to the strap and positionable in a first, in-use configuration wherein the case is substantially flattened for wearing behind the user's head, and in a second, storage configuration wherein the case envelops at least the mask lens. The case may include a gusset structure interposed between the front and rear panels to increase the volume of the case in the storage configuration.

In accordance with another aspect of the invention, a case is adapted for a mask including a frame configured to fit sealingly around a portion of a user's face, at least one lens supported in the frame, and first and second strap attachment structures for receiving and cooperating with an attachment strap to maintain the mask securely on the user's head, one attachment structure being disposed on either side of the frame. The case includes flexible front and rear panels, and first and second straps. The front panel is configured to bear against the back of the user's head when worn, while the rear panel is secured to the front panel and defines with the front panel an invertible pouch. The rear panel further defines an opening through which the mask may be inserted into and removed from the pouch. The first and second straps are configured for attachment to the first and second strap attachment structures respectively. The first strap is secured to a first side region of the pouch and extends from the pouch toward the mask when secured to the first strap attachment structure. The second strap is secured to a second side region of the pouch opposite from the first side region and extends from the pouch toward the mask when secured to the second strap attachment structure. In a particularly preferred embodiment, the first and second straps are elastic members. Also, the first and second straps preferably include a hook and loop fastening system defined by regions which overlie one another when the mask and case are worn by the user.

The invention also provides a convertible mask case including a flexible first panel, a flexible second panel secured to the first panel and a strap system. The second panel defines with the first panel a convertible pouch. The pouch includes an opening through which the mask may be inserted into and removed from the pouch. The strap system includes first and second strap portions configured for attachment to the pouch and to the first and second strap attachment structures respectively. The first and second strap portions extend between the pouch and the first and second attachment structures when the mask and pouch are worn around the user's head. The pouch is collapsible into a first, worn configuration wherein the pouch fits securely against the user's head and a second, storage configuration wherein the pouch envelopes over the mask to cover at least the lens.

In accordance with still another aspect of the invention, a case is adapted to cover at least the front and contiguous surfaces of a mask, including the outer surface of the primary and secondary lenses, while not completely enclosing the mask. The most important but vulnerable parts of the mask with respect to visibility are thereby substantially protected while in storage, while the interior portions of the mask remain uncovered whereby they may dry more quickly in the surrounding air. In this embodiment of the invention, as in the others, the case may be left secured to the mask and used as a cushioned strap encircling the back of the user's head for holding the mask upon the user's face.

Yet another aspect of the invention relates to a method of protecting a mask such as a diving or skiing mask while the mask is in storage by enclosing it within a flexible or semi-flexible pouch, the pouch being formed by reconfiguring the walls of a cushion for a strap, the cushion including a plurality of walls fabricated of a fabric, elastomeric, or similar flexible material in sheet form, the strap being disposed around the back of the user's head for the securing of the mask to the user's face when the mask is in use, the cushion being used to distribute load of the strap to a relatively large area upon the back of the user's head to increase comfort of the strap.

In accordance with one aspect of the invention a mask and case combination includes a mask having a frame configured to fit sealingly around a portion of a user's face. At least one lens supported is in the frame. The combination also includes a case having a flexible front panel and a flexible rear panel secured to the front panel. The rear panel and front panel define a pouch having an opening through which the mask may be inserted into and removed therefrom. A first strap is attached to a first side region of the pouch and extends from the pouch toward the mask. The first strap is also attached to a first side of the mask. A second strap is attached to a second side region of the pouch opposite from the first side region. The second strap extends from the pouch toward the mask and is attached to a second side of the mask. The case is collapsible into a first, worn configuration in which the case bears against the user's head. In a second, storage configuration the mask is stored within the pouch such that the at least one lens is covered by the cover. In the second storage configuration, the first and second straps remain attached to the first and second sides of the mask and case respectively. The straps are substantially clear of a region intermediate the first and second sides of the mask when the mask is in the storage configuration. In one embodiment the case includes central gusset. The gusset being attached to the front panel and to the rear panel such that it is foldable into a collapsed position between the front and rear panels. In another embodiment the front panel includes upper and lower panel portions, the opening being defined between the upper and lower panel portions. The front panel bears against the user's head in the worn configuration.

In another aspect of the invention a convertible case and a mask combination include a mask having a frame configured to fit securely around a portion of a user's face. At least one lens is supported in the frame. The frame has a right side and a left side. The mask includes a right and a left strap attachment structure disposed on the right and left sides of the frame respectively. A case includes a flexible first panel and a flexible second panel secured to the first panel. The second panel defines with the first panel a convertible pouch, the pouch has an opening through which the mask may be inserted into and removed from the pouch. The pouch has a right and left side. A strap system includes right and left strap portions configured for attachment to the right and left side of the pouch and to the right and left strap attachment structures respectively. The right and left strap portions extend between the pouch and the right and left attachment structures when the mask and pouch are worn around the user's head. The pouch is collapsible into a first, worn configuration wherein the pouch fits securely against the user's head. In the worn configuration the left and right sides of the frame, and the left and right sides of the pouch are proximate the left and right sides of the user respectively. In a second, storage configuration the left and right portions of the mask fit within the left and right sides of the pouch respectively.

Yet another aspect of the invention a mask includes a front lens having an outward surface. A case includes a first flexible panel and a second flexible panel, the first and second panels defining a pouch therebetween. The pouch has an opening to receive the mask. A first strap extends between and connects the right side of the case and the right side of the mask, and a second strap extends between and connects the left side of the case and the left side of the mask. In a first, worn configuration the case bears against the user's head to secure the mask to the user's face. In this worn configuration, the left and right sides of the mask and the left and right sides of the case are proximate the left and right sides of the user respectively. In a second, storage configuration the mask and case are rotated relative to each other, such that the left and right sides of the mask fit within the left and right sides of the pouch respectively. Further, in the storage configuration, the outward surface of the front lens is adjacent a portion of the case distal the opening.

BRIEF DESCRIPTION OF THE DRAWINGS

The present invention will become more fully understood from the following detailed description, taken in conjunction with the accompanying drawings, wherein like reference numerals refer to like parts, in which:

FIG. 1 is a perspective view of a flexible case in accordance with a first preferred embodiment, the case being slidingly received over a portion of a strap of a mask supported on a user's head;

FIG. 2 is a front elevational view of the case of FIG. 1 shown in its folded position and illustrating panels defining an opening for inserting the mask therein, in their joined or closed position;

FIG. 3 is a sectional view along line 3—3 of FIG. 1 illustrating a preferred construction of the case;

FIG. 4 is a sectional view along line 4—4 of FIG. 1, illustrating the internal construction of the case;

FIG. 9 is a sectional view of the case of FIG. 8 along line 9—9, illustrating the several components of this embodiment;

FIG. 10 is a perspective view of the case of FIG. 8 in a first phase of inversion for insertion of the mask therein;

FIG. 11 is a perspective view of the case of FIG. 8 following full insertion of the mask therein;

FIG. 12 is a sectional view of the case of FIG. 11 along line 12—12, showing the mask fully inserted into the case;

FIG. 13 is a front perspective view of a second preferred embodiment of the invention, wherein a pair of straps are permanently secured to either side of the case;

FIG. 14 is a sectional view of the case of FIG. 13 along line 14—14, illustrating a preferred construction of this embodiment;

FIG. 15 is a perspective view of the embodiment of FIG. 13 shown attached to a mask;

FIG. 16 is a back elevation view of the case of FIG. 13 illustrating a preferred arrangement of the attachment straps and showing the panels of the case defining its opening in their joined position;

FIG. 17 is a perspective view of the case of FIG. 13 closed over a mask;

FIG. 18 is a perspective view of the case of FIG. 17 removed from the mask and partially folded into its storage position;

FIG. 24 is a back elevation view of a third preferred embodiment of the inventive case wherein the opening is defined along one edge of the pouch;

FIG. 25 is a sectional view of the case of FIG. 24 along line 25—25 of FIG. 24, illustrating the construction of the case;

FIG. 26 is a sectional view of the case of FIG. 24 along line 26—26, illustrating the internal components of the case when in their folded position;

FIG. 27 is a perspective view of the case of FIG. 24 during a first phase of insertion of a mask therein;

FIG. 31 is a sectional view of the case of FIG. 30 along line 31—31;

FIG. 32 is a sectional view of the case of FIG. 30 along line 32—32;

FIG. 33 is a perspective view of the case of FIG. 30 during a first phase of insertion of a mask therein;

FIG. 34 is a perspective view of the case of FIG. 33 with the mask fully enveloped by the case;

DETAILED DESCRIPTION OF PREFERRED EMBODIMENTS

Figure 5:
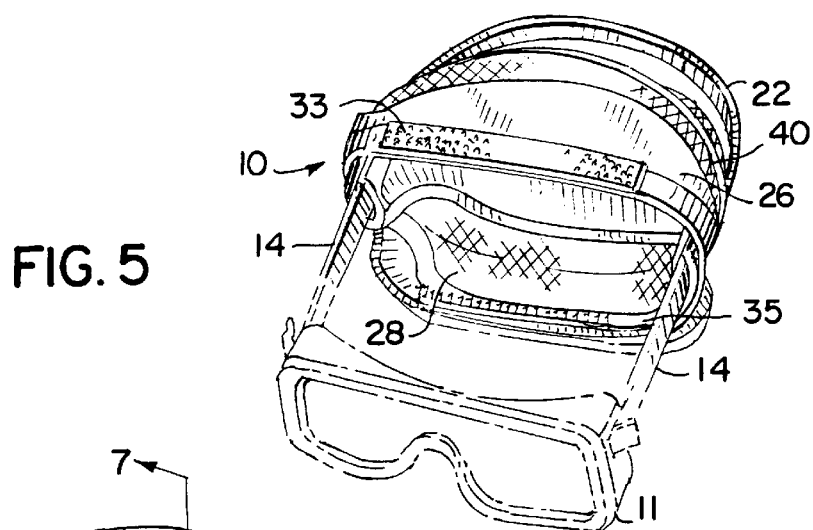
FIG. 5 is a perspective view of the case of FIG. 1 in a first phase of inversion for insertion of the mask therein.

Turning now to the figures and referring first to FIG. 1, a soft, flexible case for a mask is illustrated and designated generally by the reference numeral 10. Case 10 is shown coupled to a mask 11 via a flexible strap 14. Strap 14 extends around the head 16 of a user, positioning case 10 in a folded position tightly behind the users head 16. Mask 11 may be of any conventional type, including a shell or frame 12 made of a soft flexible material supporting a lens 13. In use as illustrated in FIG. 1, strap 14 holds shell 12 of mask 11 firmly against the user's face to seal the mask and prevent the intrusion of water behind lens 13. Ends 18 of strap 14 are secured to attachment ring assemblies 20 on either side of the mask. Ring assemblies 20 may be of any known type, and generally provide for adjustability of tension of strap 14 by doubling the end of the strap back upon itself such that the end of strap 14 exits toward the rear of attachment ring assembly 20. In the folded, cushioning position illustrated in FIG. 1, case 10 is secured along a central region 22 of strap 14 located behind the user's head 16.

Referring now more specifically to the preferred construction of the first embodiment illustrated in FIGS. 1 through 7, case 10 includes a front panel 24 attached to upper and lower rear panels 26 and 28, respectively. A front border strip 30 extends around a peripheral of front panel 24, while a similar rear border strip 31 extends around both upper and lower rear panels 26 and 28. Upper and lower rear panels 26 and 28 meet in a central region and overlap one another, defining an opening 32 in the rear of case 10 through which mask 11 may be inserted and removed as described more fully below. A first closure element, preferably in the form of a hook and loop closure panel 33, is provided along an inner lower edge 34 of upper rear panel 26. A cooperating closure element 35, also preferably a hook and loop closure panel, is provided along an outer upper edge 36 of lower rear panel 28 in facing relation to element 33, providing a positive closure means for case 10 both in the folded configuration illustrated in FIGS. 1–4 as well as in an inverted, storage position described below in reference to FIGS. 6 and 7. In addition to opening 32, the embodiment of case 10 illustrated in FIGS. 1 through 12 includes left and right side apertures 38 through which strap 14 is slidingly inserted upon assembly of case 10, strap 14 and mask 11. Front and rear panels 24, 26 and 28 thus define an invertible pouch for storage of mask 11 as described below.

FIGS. 3 and 4 illustrate a preferred construction of the elements described above, in addition to a central gusset 40 preferably provided in case 10 to readily expand its internal capacity. As shown in FIG. 3, front panel 24 is joined, such as by stitching, to a front gusset panel 42 which has a generally elongated annular shape, while rear panels 26 and 28 are joined to a similar rear gusset panel 44. A front border hem 46 is thus formed along upper and lower regions along which front panel 24 and front gusset panel 42 are joined, with front border 30 being captured around the joint of these two panels by the same stitching. Front gusset 42 is joined to a rear gusset panel 44 along a gusset hem 48. Rear gusset panel 44 is, in turn, joined to upper and lower rear panels 26 and 28, such as by a border hem 50, which preferably also captures rear border 31 and holds border 31 in place around the joint. As will be appreciated by those skilled in the art, gusset hem 48 is discontinuous in the region of side apertures 38 in order to provide a gap between gusset panels 42 and 44, thereby defining apertures 38. As shown in FIGS. 3 and 4, when assembled with strap 14, case 10 extends along strap 14 and is stretched and flattened somewhat by tension of strap 14 when pulled taut behind the user's head. However, strap 14 remains somewhat free to stretch through side apertures 38.

Front panel 24, rear panels 26 and 28, gusset panels 42 and 44, and borders 30 and 31 are all preferably made of flexible sheet materials, such as fabrics, synthetic composite materials and the like. In a particularly preferred embodiment, front panel 24 is made of an open or close-cell neoprene, as are rear panels 26 and 28. Gusset panels 42 and 44 may be made of a lighter-weight synthetic fabric, or may comprise open netting. As will be appreciated by those skilled in the art, the use of synthetic foam materials, such as neoprene for front and rear panels 24, 26 and 28 provides added buoyancy to case 10, preferably sufficient to maintain mask 11 afloat, or at least to significantly reduce the tendency of mask 11 to sink in water (e.g., when case 10 is used with a diving mask and the mask is inadvertently dropped by a diver). In addition, the use of light-weight synthetic fabrics for gusset panels 42 and 44 allows case 10 and mask 11 to dry quickly once removed from the water and stored in their storage position as described below. Moreover, it should be noted that the use of foam-type materials for front panel 24 provides a cushion for added comfort against the user's head when in use, while the use of relatively light-weight materials for gusset panels 42 and 44 reduces the overall thickness of case 10 when in its folded, in-use position as shown in FIGS. 1 through 4.

Figure 6:
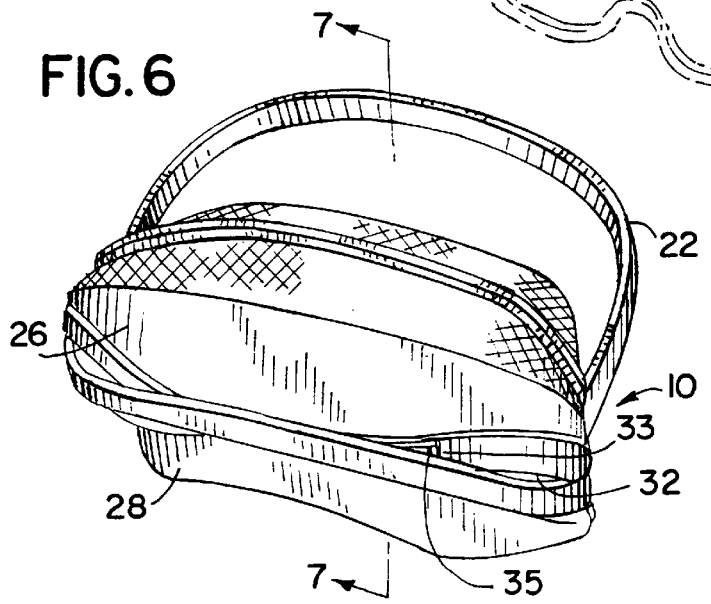
FIG. 6 is a perspective view of the case following insertion of the mask therein.
Figure 7:
FIG. 7 is a sectional view of the case along line 7—7 of FIG. 6, showing the configuration of the case when the mask is lodged or stored therein, and illustrating the manner in which the opening of the case is closed over the mask.

Following use of mask 11, a user inserts mask 11 into case 10 as follows. As best illustrated in FIG. 5, the user first separates closure elements 33 and 35, such as by pulling upper and lower rear panels 26 and 28 apart. Borders 30 and 31 are then pressed inwardly and upper and lower rear panels 26 and 28 are folded back over the borders, effectively inverting case 10 on itself and expanding central gusset 40. Mask 11 is then moved rearwardly into the pouch defined by the now inwardly facing exterior panels of case 10. Central region 22 of strap 14 may be pulled rearwardly, sliding strap 14 through side apertures 38 to further draw mask 11 into case 10. Once mask 11 is fully enveloped by case 10, upper and lower rear panels 26 and 28 may be pulled toward one another as shown in FIG. 6. It should be noted that due to the inversion of case 10 as it is converted from its folded, in-use position to its storage position, closure elements 33 and 35 once again are located in a mutually facing and cooperating position and may be rejoined as shown in FIG. 6. As best illustrated in FIG. 7, once inverted and closed around mask 11, exterior features of case 10 will be located in an interior region of the case. Thus, front and rear borders 30 and 31 bound mask 11 and upper and lower rear panels 26 and 28 are rejoined over mask 11, thereby protecting the mask lens from damage through inadvertent contact with other equipment. It should also be noted that in the embodiment illustrated in FIGS. 1 through 7, central region 22 of strap 14 is located outside case 10 when placed in its storage position; thus, the user may grasp strap 14 for transport of case 10 with mask 11 or may use strap 14 for hanging the case from convenient hooks or the like.

Figure 8:
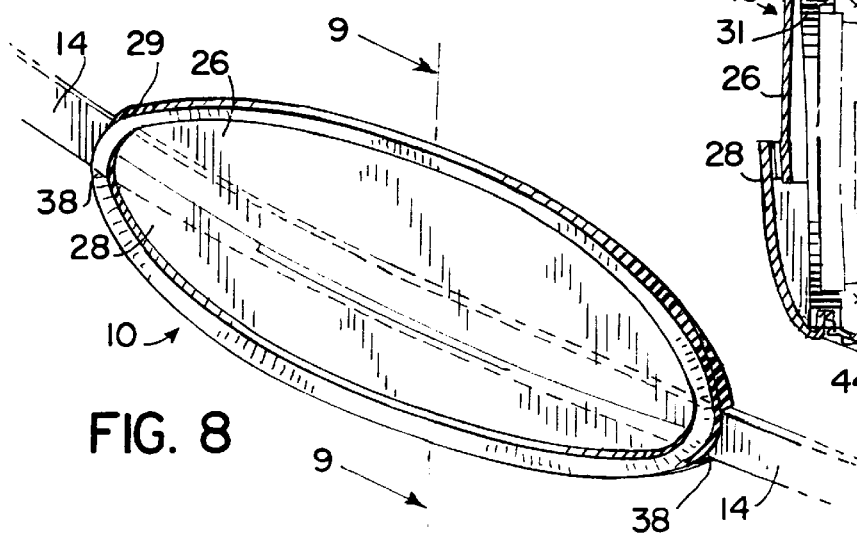
FIG. 8 is a perspective view of a variant of the first preferred embodiment, wherein the construction of the case is simplified.

FIGS. 8 through 12 illustrate a variant of the case described above wherein central gusset 40 is essentially eliminated. Thus, as shown in FIGS. 8 and 9, case 10 includes a front panel 24 and upper and lower rear panels 26 and 28 bounded by a single border strip 29. While border strip 29 preferably completely surrounds both front panel 24 and rear panels 26 and 28, border 29 and the front and rear panels are separated along end regions corresponding to side apertures 38, permitting passage of strap 14 therethrough as described above. A single border hem 45 is preferably provided for joining front panel 24 to rear panels 26 and 28 and for capturing border 29 around the region where these panels are joined. Closure elements 33 and 35 are provided along lower edge 34 and upper edge 36 of upper and lower rear panels 26 and 28, respectively. As in the previous embodiment, these closure elements are preferably hook and loop fastener strips secured to the rear panels, such as by gluing, stitching or any other suitable means. Case 10 is assembled with strap 14 as before, by passing strap 14 through apertures 38 and lodging a central region 22 of strap 14 within case 10 in its folded, in-use configuration shown in FIGS. 8 and 9. Following use, when a user desires to store mask 11 within case 10, closure elements 33 and 35 are separated from one another, and upper and lower rear panels 26 and 28 are folded up over border 29 in order to invert case 10, as illustrated in FIG. 10. Strap 14 may then be pulled rearwardly to draw mask 11 into case 10. The case may then be closed over the mask and closure elements 33 and 35 may again be joined as shown in FIG. 11. As in the previous embodiment, external features of case 10 are located within the interior of the case when placed in its storage position, as shown in the sectional view of FIG. 12. Thus, border 29 generally bounds mask 11 and closure elements 33 and 35 secure upper and lower rear panels 26 and 28 to one another to maintain these panels in a protective position over mask 11.

In an alternative configuration of case 10, illustrated in FIGS. 13 through 23, fastening strips may be secured directly to case 10 in order to define a padded case and attachment system, obviating the need for a separate strap as in the previous embodiments. Thus, in an alternative preferred embodiment illustrated in FIG. 13, case 10 includes first and second attachment straps 52 and 54, respectively, permanently secured to case 10, such as by stitching along attachment regions 56. The general construction of case 10 in this embodiment may be substantially identical to that described above with reference to FIGS. 1 through 7, except that front panel 24 and upper and lower rear panels 26 and 28 may be completely joined along side regions, thereby eliminating side apertures 38 from the previous embodiment. Instead, at similar locations of case 10, attachment regions 56 define points of anchoring for attachment straps 52 and 54. Other features, such as front panel 24, rear panels 26 and 28 and gusset panels 42 and 44, along with borders surrounding these panels and their corresponding hems, may be substantially identical to those described with regard to the previous embodiment, as illustrated in the sectional view of FIG. 14.

Figure 19:
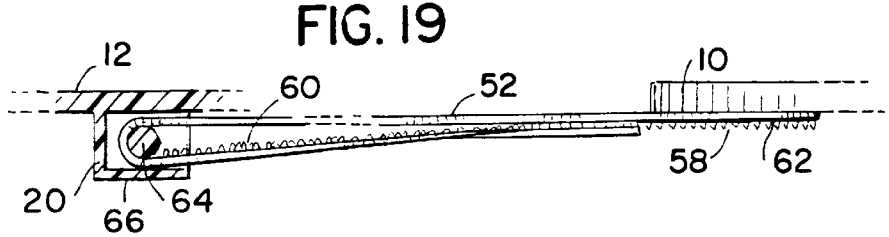
FIG. 19 is a sectional view of the case of FIG. 13 along line 19—19 of FIG. 15, illustrating a preferred method for attaching the mask to an attachment point of a mask.

FIGS. 15 and 16 illustrate a preferred arrangement for securing attachment straps 52 and 54 to mask 11. As best shown in FIG. 16, each attachment strap preferably includes a first region 58 defining a first type of attachment mechanism, such as a hook-type attachment region, and a second region 60 distal from case 10 with respect to regions 58, defining a second, cooperating attachment structure, such as a loop-type attachment strip. Regions 58 and 60 are designed to be located along an outer side 62 of straps 52 and 54 and are located in mutually facing relation when attached to mask 11 as shown in FIG. 15. As illustrated in that figure, straps 52 and 54 are attached to mask 11 by routing the strip first through an attachment assembly 20 provided on either side of mask 11, and folding straps 52 and 54 back toward case 10 so that region 60 of each strip at least partially overlies region 58, permitting attachment of these regions to one another. FIG. 19 provides a sectional view along line 19-19 of FIG. 15 illustrating this attachment system. As shown in FIG. 19, attachment assembly 20 may conveniently include a post 64 at least partially surrounded by a shroud 66. Straps 52 and 54, secured to case 10, are passed around post 64 and folded back toward case 10 to bring regions 58 and 60 into alignment. In a particularly preferred embodiment, straps 52 and 54 are made of an elastic material or an elasticized fabric to which regions 58 and 60 are either applied, such as by gluing or stitching, or on which regions 58 and 60 are directly formed. Such elastic materials provide a comfortable yet snug fit for mask 11 on the user's head, while holding case 10 securely in place during use of mask 11.

In this embodiment of case 10, insertion of mask 11 into the case for storage results in enclosing both mask 11 and straps 52 and 54 within case 10. Thus, as shown in FIG. 17, insertion of mask 11 into case 10 begins, as before, by separation of closure elements 33 and 35 from one another and by inversion of case 10 to expand central gusset 40 outwardly. Mask 11 may then be inserted into inverted case 10, along with attachment strips 52 and 54. Once fully inserted into case 10, mask 11 may be enveloped by the case and closure elements 33 and 35, once again in mutually facing relation, may be joined to completely enclose mask 11 within the case, as illustrated in FIG. 18.

Figure 20:
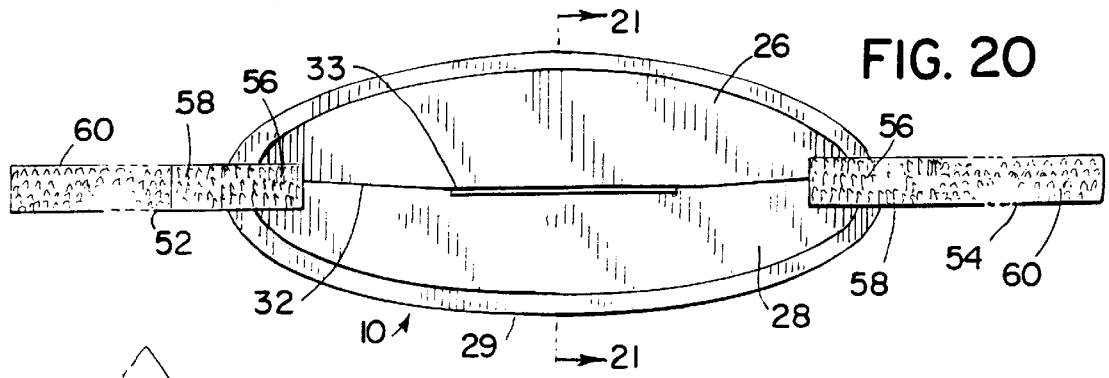
FIG. 20 is a back elevation view of a variant of the second embodiment of FIG. 13.
Figure 21:
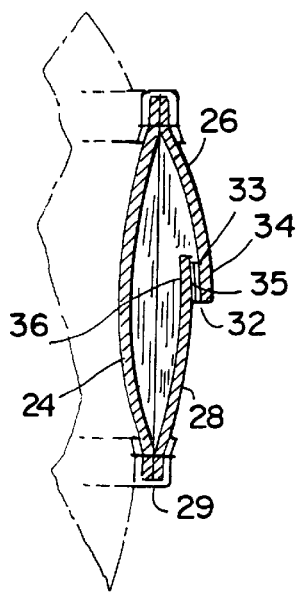
FIG. 21 is a sectional view along line 21—21 of FIG. 20 illustrating the various components of this configuration of the case.
Figure 22:
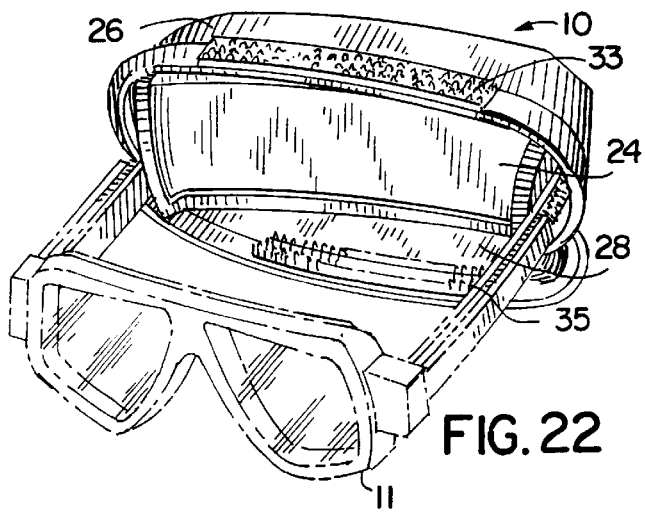
FIG. 22 is a perspective view of the case of FIG. 20, partially inverted for insertion of the mask therein.
Figure 23:
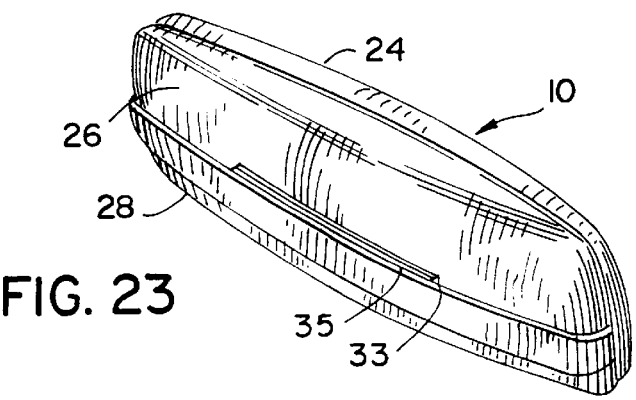
FIG. 23 is a perspective view of the case of FIG. 20 fully closed around the mask.

A variant to the latter embodiment is illustrated in FIGS. 20 through 23, wherein gusset elements are eliminated to reduce the overall thickness of case 10. Thus, as shown in FIGS. 20 and 21, case 10 may be formed of a front panel 24 and upper and lower rear panels 26 and 28 bounded by a single border 29. Closure elements 33 and 35 are provided along lower and upper edges 34 and 36 of panels 24 and 26, respectively, as before. Attachment strips 52 and 54 are secured to attachment regions 56 on either side of case 10 and are configured as described above, including hook regions 58 and loop regions 60 disposed so as to lie in mutually facing relation when attached to attachment assemblies 20 on either side of mask 11. FIGS. 22 and 23 illustrate stages of insertion of mask 11 into case 10 in accordance with this embodiment. As before, insertion of the mask into case 10 begins with separation of closure elements 33 and 35 and inversion of case 10 as shown in FIG. 22. Mask 11 may then be pressed into inverted case 10 and closure elements 33 and 35, once again in mutually facing relation, may be closed over mask 11 to fully envelop the mask and close the case as shown in FIG. 23.

FIGS. 24 through 29 represent another preferred embodiment of the inventive case wherein an opening for insertion and removal of the mask is provided along an edge of the pouch. Thus, as best shown in FIGS. 24, 25 and 26, case 10 includes a front panel 24 secured along an upper edge to a rear panel 26. In this embodiment, an integral gusset structure is defined by inner panels 70 and 72 which are interposed between front and rear panels 24 and 26. Inner panels 70 and 72 are preferably a loose net material or a lightweight fabric which promotes drying of mask 11 when placed within case 10 as described below. Front panel 24 and rear panel 26 are joined along their upper edges and preferably surrounded by a border 30 in the manner described above with reference to the previous embodiments. Along its lower edge, front panel 24 is joined to inner panel 70, while rear panel 26 is joined to inner panel 72. Borders 74 and 76 preferably enclose the edges of panels 24 and 70, and 26 and 72, respectively. Side apertures 38 are formed between panels 24, 70 and 26, 72, as best illustrated in FIG. 25. Apertures 38 permit passage of a strap 14 through case 10 as described above. Moreover, edge borders 78 and 80 are preferably sewn along loose edges of inner panels 70 and 72. Hook and loop closure panels 33 and 35 are secured along these edges for maintaining inner panels joined with in the folded position illustrated in FIGS. 24–25 as well as in the protective position shown in FIGS. 28 and 29. In this embodiment, opening 32 is defined between front and rear panels 24 and 26.

Figure 28:
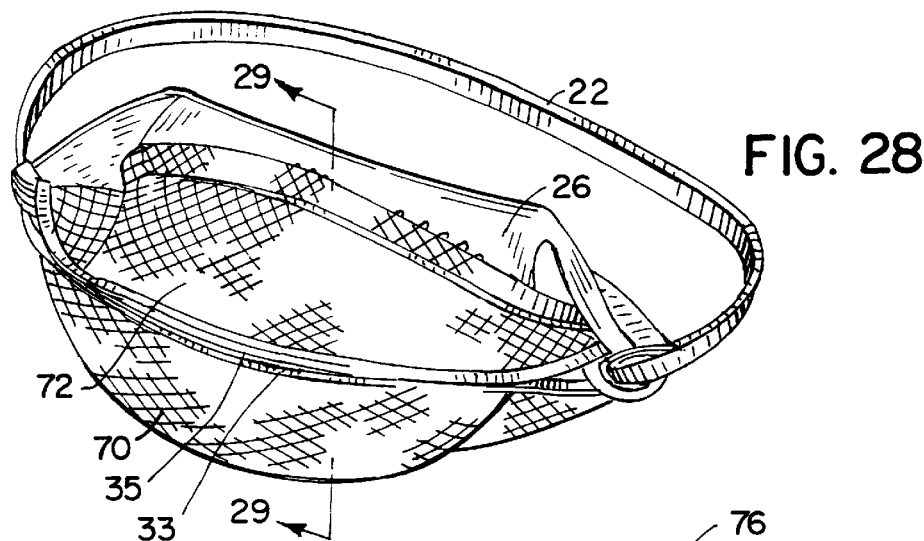
FIG. 28 is a perspective view of the case of FIG. 24 with the mask fully inserted therein.
Figure 29:
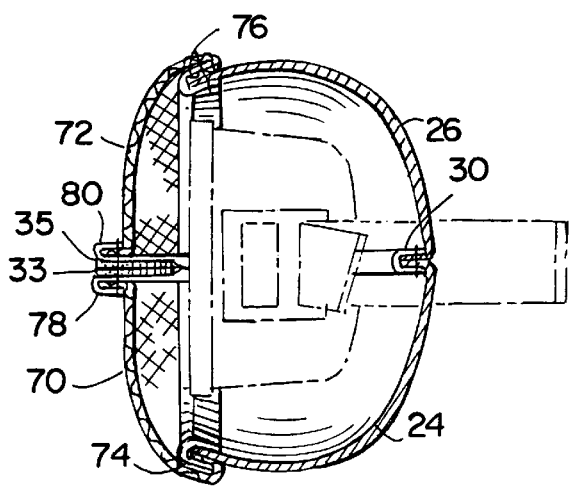
FIG. 29 is a sectional view of the case of FIG. 28 along line 29—29 showing the orientation of the mask within the closed case.
Figure 30:
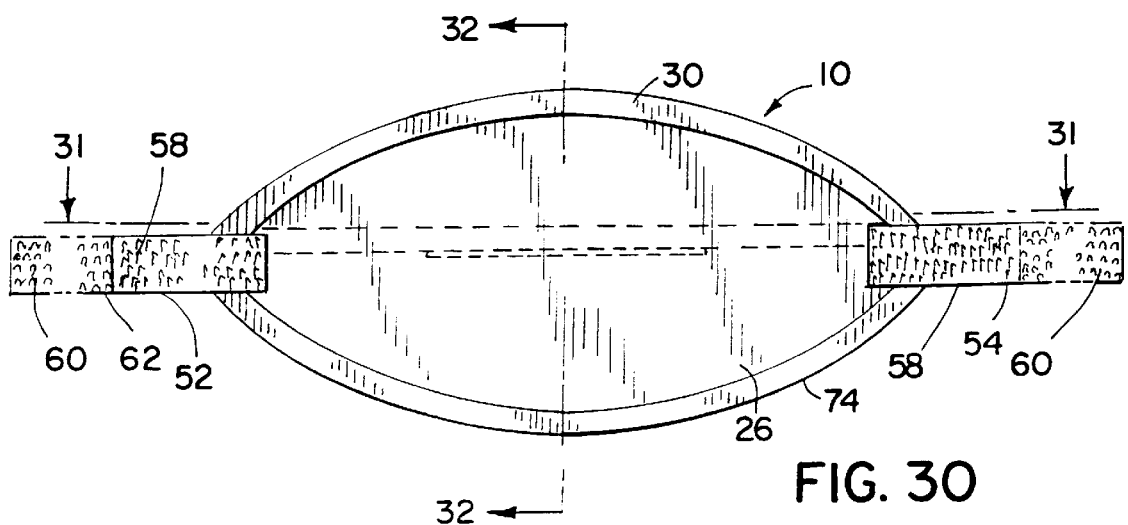
FIG. 30 is a back elevation of a variant of the third embodiment wherein straps are secured to the pouch for subsequent attachment to a mask.

Stages of insertion of mask 11 into case 10 are illustrated in FIG. 27 and 28. As shown in FIG. 27, case 10 is first opened by drawing inner panels 70 and 72 out of the pouch formed by front and rear panels 24 and 26. Closure panels 33 and 35 are detached from one another and the case is inverted and drawn along strap 14 toward mask 11. Mask 11 is then inserted into case 10 and closure panels 33 and 35 may be rejoined, completely enclosing mask 11 within case 10 as best shown in FIG. 29.

FIGS. 30 through 34 represent a variant of the embodiment just described. In this embodiment, rather than apertures 38 for a separable strap 14, first and second attachment straps 52 and 54 are provided, similar to the arrangement described above with reference to FIGS. 13 through 23. In this embodiment, the components of case 10 in this embodiment are essentially identical to those described above with reference to FIGS. 24–29, including front and rear panels 24 and 26, and inner panels 70 and 72 (see FIGS. 30–32). However, attachment straps 52 and 54 are secured to rear panel 26, such as by stitching in attachment regions 56. Hook and loop attachment regions 58 and 60 are provided along an outer side of straps 52 and 54 in locations allowing these regions to lie in mutually facing relation to one another when straps 52 and 54 are attached to a mask 11 as shown in FIG. 33.

Mask 11 is inserted into case 10 in this embodiment as shown in FIGS. 33 and 34. First, case 10 is inverted by drawing inner panels 70 and 72 out of the pouch formed by front and rear panels 24 and 26, detaching closure panels 33 and 35 from one another. Mask 11 is then pressed into the open case and closure panels 33 and 35 are rejoined to close case 10 around the mask.

Figure 35:
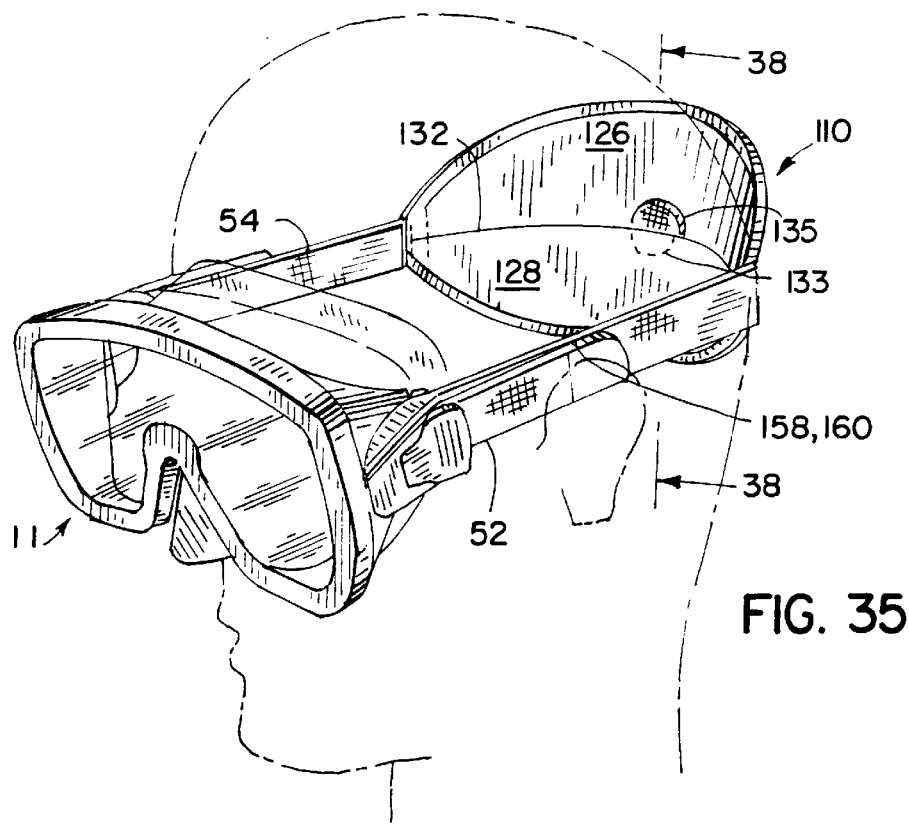
FIG. 35 is a perspective view of a flexible case in accordance with a fourth preferred embodiment, the case in use as a head band.
Figure 36:
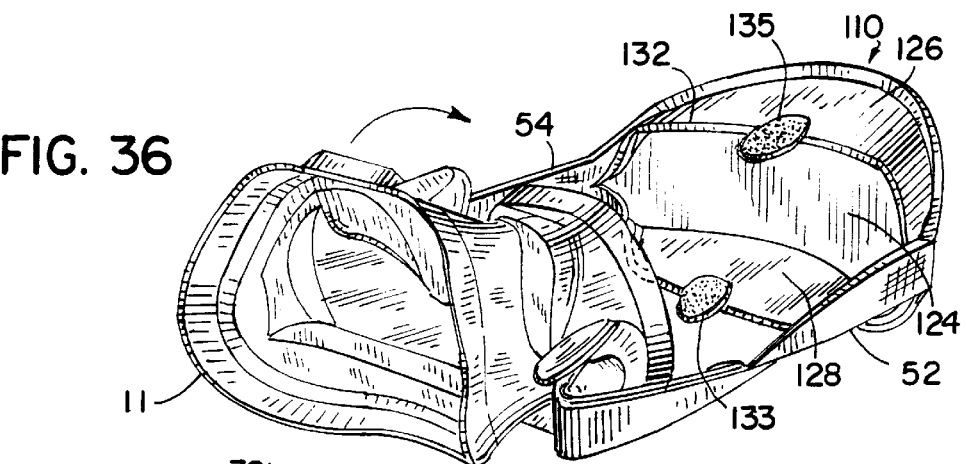
FIG. 36 is a perspective view of the case of FIG. 35 in preparation for insertion of a mask therein.
Figure 37:
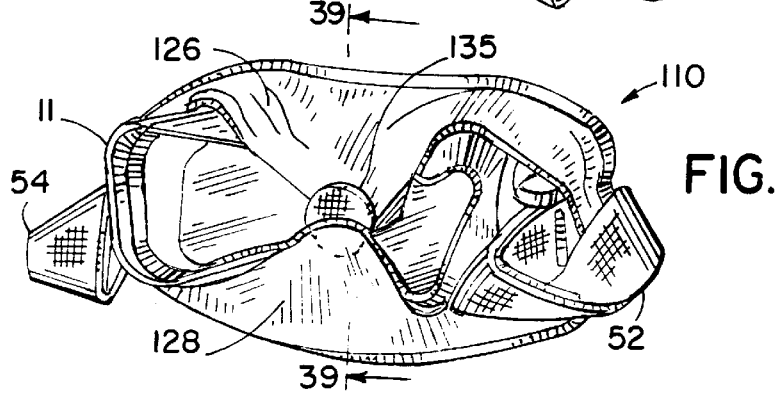
FIG. 37 is a perspective view of the case following insertion of the mask therein.
Figure 38:
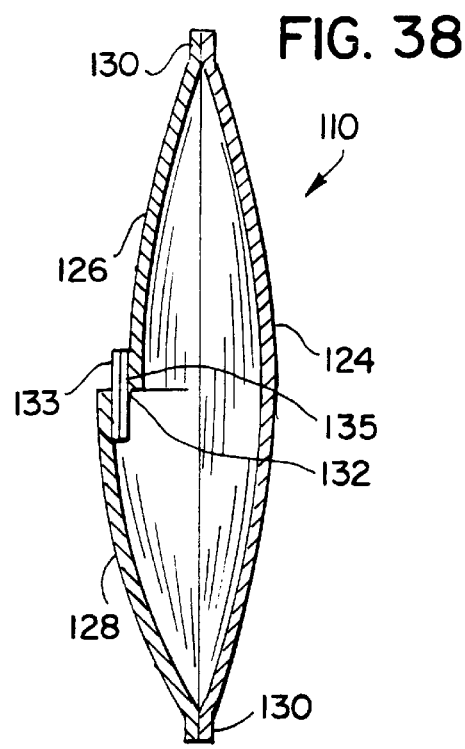
FIG. 38 is a sectional view of the case along line 38—38 of FIG. 35, showing the configuration of the case when being used as a head band.

FIGS. 35 through 39 represent still another preferred embodiment of the invention wherein an opening 132 for insertion and removal of mask 11 is provided at the juncture of a panel 126 and a panel 128. Thus, as best seen in FIGS. 36 and 38, case 110 includes an upper front panel 126 and a lower front panel 128, both secured to a rear panel 124. The upper and lower edges of rear panel 124 are joined to the adjacent edges of upper front panel 126 and lower front panel 128, defining a product edge 130. Product edge 130 may further include one of the many variations of piping or hemming well known to those skilled in the art. Upper and lower front panels 126, 128 are provided with closure panels 133, 135, whereby opening 132 may be kept closed.

Figure 40:
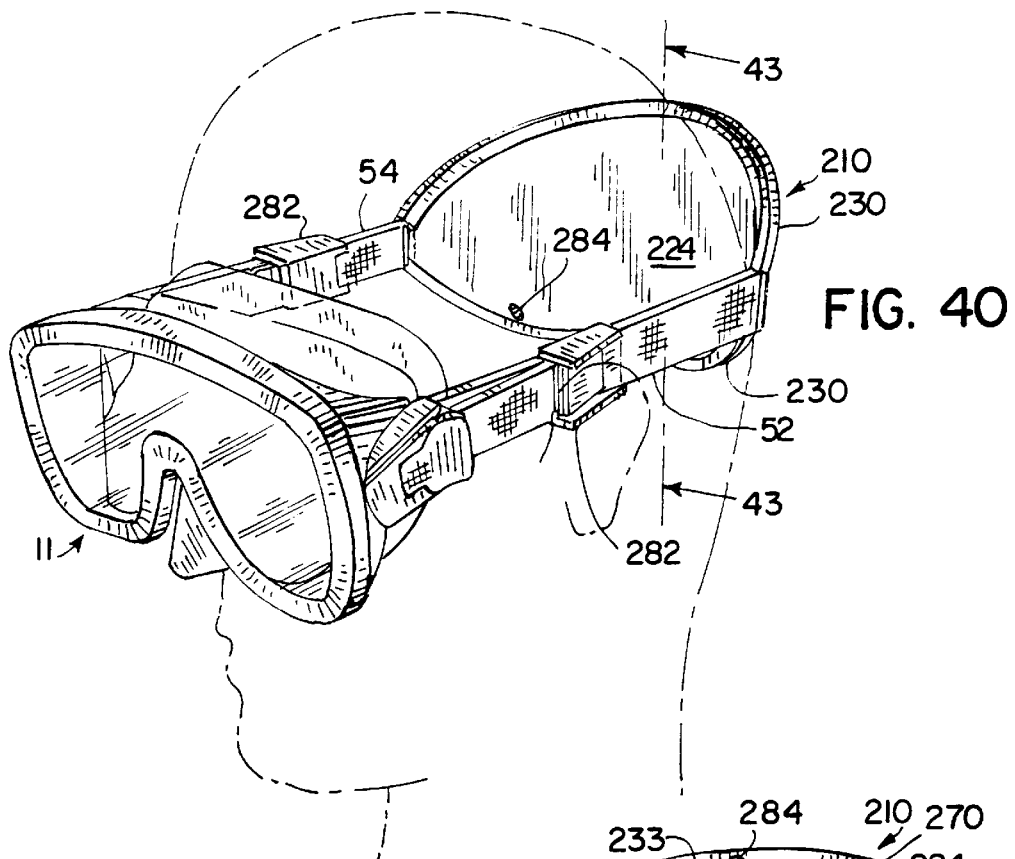
FIG. 40 is a perspective view of a flexible case in accordance with a fifth preferred embodiment, the case in use as a head band.

In this embodiment, straps 52, 54 may be provided with hook 158 and loop 160 securing panels as in the previous embodiments, or may alternatively be provided with one of the plastic or metal buckle configurations widely used and known to those skilled in the art, a presently preferred buckle being configured as a lever-operated cam 282 (shown in FIGS. 40 through 42) which clamps a portion of strap 52, 54 to an adjacent surface of strap 52, 54 and thereby holds it frictionally in a desired position.

Figure 45:
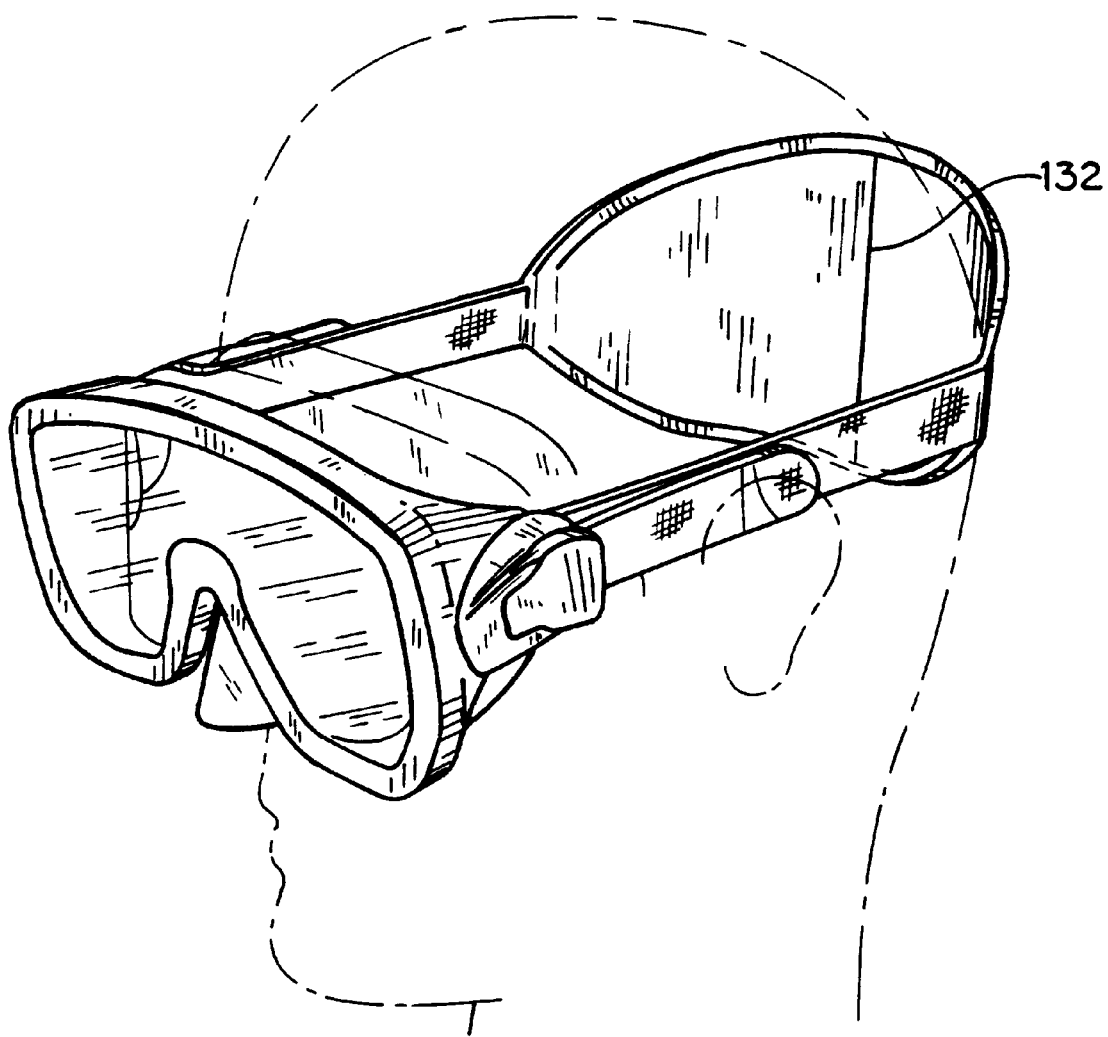
FIG. 45 is a perspective view of an alternative embodiment.

As illustrated in FIG. 35, panels 126 and 128 are adjacent to and bear against the user's head when the mask is being worn. In this worn configuration opening 132 is also adjacent the user's head. However, it is also possible for the opening 132 to be located in the rear panel 124, such that opening 132 is distal the user's head. Further as illustrated in FIG. 35, in the worn position, strap 52 is proximate the left side of the user's head and attached to the left side of mask 11, while strap 54 is proximate the right side of the user's head and attached to the right side of mask 11. In a similar manner strap 52 is attached to the left side of case 110 and strap 54 is attached to the right side of case 110. In this embodiment opening 132 is horizontal extending from the right side of case 110 toward the left side of case 110. However, opening 132 could also be a vertical opening, defined by left and right front panels (see FIG. 45) attached to rear panel 124. The left and right front panels may be distinct and separte panels or may be defined by a slit in the front panel. The slit may extend the entire vertical distance or may extend only a portion of the distance between the top and bottom of the front panel. As noted above, the opening could be configured to be on either the portion of the case that bears against the user's head, or the opposite side thereto when being worn.

FIG. 36 best illustrates case 110 in readiness for covering of mask 11. Closure panels 133, 135 have been separated from each other, and opening 132 has been enlarged by separating upper and lower front panels 126, 128. To insert the mask 11 into case 110, mask 11 is rotated 180 degrees about its horizontal axis (see arrow in FIG. 36) so that, upon insertion into opening 132 of case 1 10, the primary front lens adjacent and covered by rear panel 124. In this configuration the left side of mask 11 is adjacent and covered by the left side of case 110, while the right side of mask 11 is adjacent and covered by the right side of case 110. Straps 52 and 54 remain on the left and right sides respectively of case 110 and mask 11. As shown in FIGS. 36 and 37 rotation of mask 11 results in each of straps 52 and 54 having a twist therein. When mask I 1 is stored in case 110, each strap 52, 54 remains external to case 110 to the extent that they do not come between rear panel 124 and the front lens of mask 11.

In the embodiment, where opening 132 is in the rear panel 124, such that opening 132 is situated distal the user's head, then both mask 11 and case 110 are rotated 180 degrees about their respective horizontal axes to permit insertion of mask 11 into case 110 through opening 132. Of course it is possible to rotate only one of the mask and case to accomplish the same final position, of the outward surface of the lens facing the opening. As above, the front lens of mask 11 is located adjacent rear panel 124. This configuration (not shown) would result in eliminating the twist in straps 52 and 54. In this embodiment, the top portion of the case is proximate the top portion of the case, while in the embodiment described immediately above, where only the mask is rotated, the top portion of the mask is proximate the bottom portion of the case.

FIG. 37 depicts the partial covering of mask 11 by case 110 in this embodiment, wherein rear panel 124 covers the front of the mask, including the front surface of the primary lens, and the outer surfaces of secondary lenses as well as contiguous portions of side, top, and bottom surfaces, thereby protecting them from scratching and marring while mask 11 is in storage. Upper and lower front panels 126, 128 extend over a portion of the side, top, and bottom surfaces of the secondary lenses as well as of a portion of the rear area of mask 11 to a degree sufficient for closures 133, 135 to be engaged with each other, whereby mask 11 is held between rear panel 124 and the pair of front panels 126, 128, while leaving a relatively large open area for entry and egress of air to promote evaporation of moisture from within mask 11.

Figure 39:
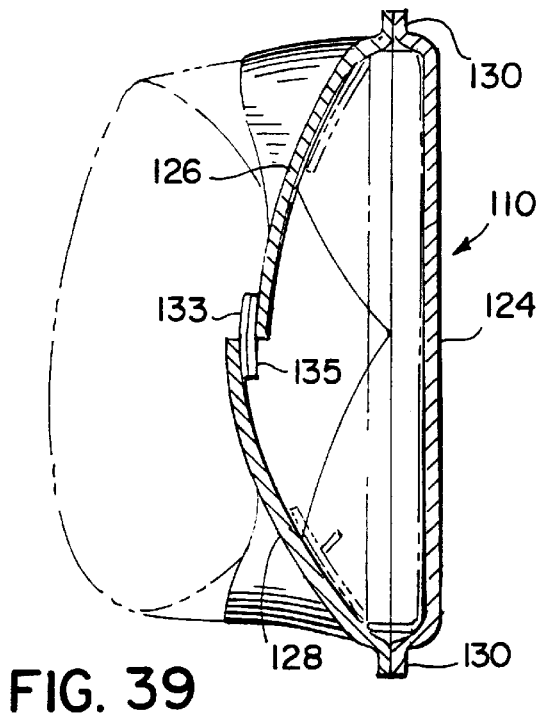
FIG. 39 is a sectional view of the case along line 39—39 of FIG. 37, showing the configuration of the case when being used to store a mask.

In FIG. 38, case 110 is depicted in cross section while mask 11 is in use and case 110 is being used as a head band to secure mask 11 to the user's face. The relatively large area of front panels 126, 128 and the total thickness of panels 126, 128 combined with rear panel 124 distribute and cushion the load of straps 52, 54 (shown in FIG. 135) upon the rear surface of the user's head. For clarity, panels 124, 126, and 128 are shown in an exaggerated relaxed condition as though case 110 were not yet placed upon the user's head and straps 52, 54 were not yet under tension and thereby causing the panels to be drawn into contact with each other. Referring now to FIG. 39, which is a cross sectional view of a case 110 covering a mask 11, the manner of holding case 110 upon mask 11 and the relationship of parts of case 110 may be understood. Closure 133, 135 may be used to secure mask 11 at least partially within case 110 while mask 11 is in storage within case 110.

Figure 43:
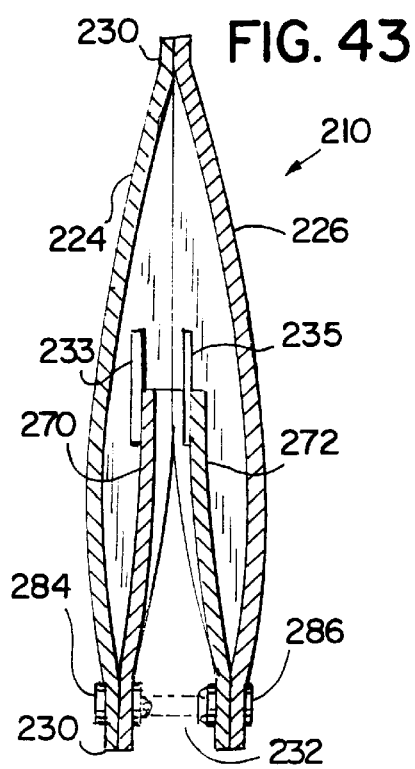
FIG. 43 is a sectional view of the case along line 43—43 of FIG. 40, showing the configuration of the case when being used as a head band.
Figure 41:
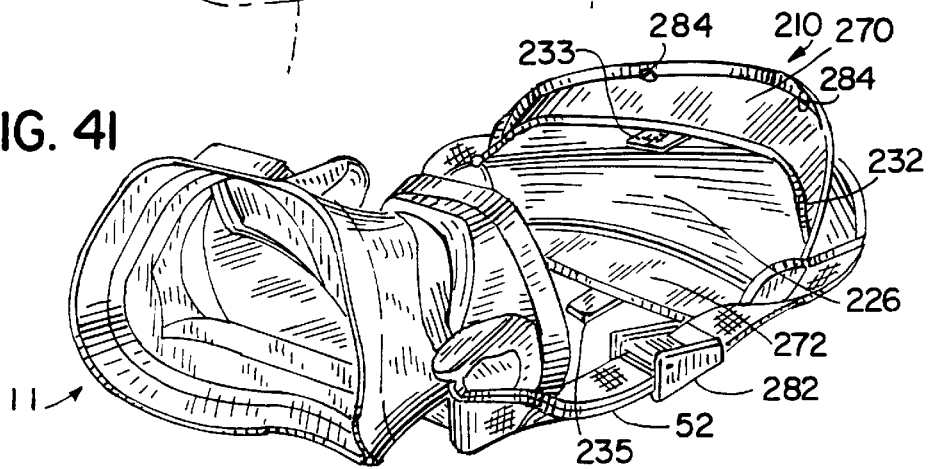
FIG. 41 is a perspective view of the case of FIG. 40 in preparation for insertion of a mask therein.

FIGS. 40 through 44 represent still another preferred embodiment of the invention wherein an opening 232 for insertion and removal of mask 11 is provided along an edge of a case 210. Thus, as best seen in FIGS. 41 and 43, case 210 includes a front panel 224 secured along an upper edge to a rear panel 226. In this embodiment, an integral gusset structure is defined by inner panels 270 and 272 which are interposed between front and rear panels 224 and 226. Inner panels 270, 272 may be fabricated of a loose net material or of a lightweight fabric which promotes drying of mask 11 when placed within case 210 as described below, or may be fabricated of a material which provides additional flotation, such as a close-cell neoprene. Front and rear panels 224, 226 are joined along their upper edges and preferably surrounded by a product edge 230 in the manner described above with reference to previous embodiments. Along its lower edge, front panel 224 is joined to inner panel 270, while rear panel 226 is joined to inner panel 272. The junctures of these panels are preferably also supplied with borders 230 as described above.

In this embodiment, straps 52, 54 may be provided with hook 158 and loop 160 securing panels as in the previous embodiments, or may alternatively be provided with one of the plastic or metal buckle configurations widely used and known to those skilled in the art, a presently preferred buckle being configured as a lever-operated cam 282 which clamps a portion of strap 52, 54 to an adjacent surface of strap 52, 54 and thereby holds it frictionally in a desired position.

FIG. 41 best illustrates case 210 in readiness for covering of mask 11. Opening 232 has been enlarged by separating front panel 224 from rear panel 226, and by then drawing inner panels 270 and 272 from within the pouch formed by panels 224 and 226. Mask 11 is then rotated 180 degrees so that the outer surfaces of its primary lenses face case 210, whereupon mask 11 is simply inserted into case 210 and closure devices, which may be hook and loop panels 233 and 235, are engaged, For best protection of the outer surfaces of the primary and secondary lenses of mask 11, mask 11 has been rotated vertically 180 degrees so that, upon insertion into opening 232 of case 210, those lens surfaces will be covered by rear panel 226.

Figure 42:
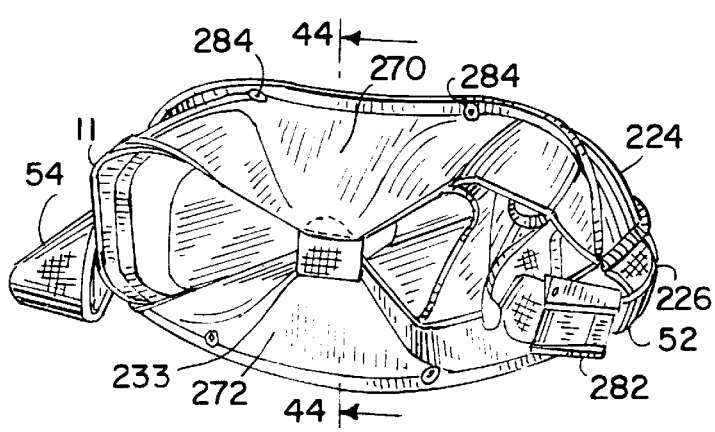
FIG. 42 is a perspective view of the case following insertion of the mask therein.

FIG. 42 depicts the partial covering of mask 11 by case 210 in this embodiment, wherein rear panel 224 covers the front of mask 11, including the front surface of the primary lens, and the outer surfaces of secondary lenses as well as contiguous portions of side, top, and bottom surfaces, thereby protecting them from scratching and marring while mask 11 is in storage. Inner panels 270, 272 extend over a portion of the rear area of mask 11 to a degree sufficient for closures 233, 235 to be engaged with each other, whereby mask 11 is held substantially between rear panel 224 and front panel 226 while leaving sufficient open area for entry and egress of air to evaporate moisture from within mask 11.

In FIG. 43, case 210 is depicted in cross section while mask 11 is in use and case 210 is being used as a head band to secure mask 11 to the user's face. For clarity, panels 224, 226, 270, and 272 are shown in an exaggerated relaxed condition as though case 210 were not yet placed upon the user's head and straps 52, 54 were not yet under tension and thereby causing the panels to be drawn into contact with each other. The relatively large area and the combined thickness of panels 224, 226 distribute and cushion the load of straps 52, 54 (shown in FIG. 40) upon the rear surface of the user's head. Closure devices (e.g., snaps 284 and 286) may be provided at the junctures of inner panels 270, 272 and outer panels 224, 226 adjacent to aperture 232 for closure of the invention when used as a head band, to inhibit a shifting or sliding of panels with respect to each other.

Figure 44:
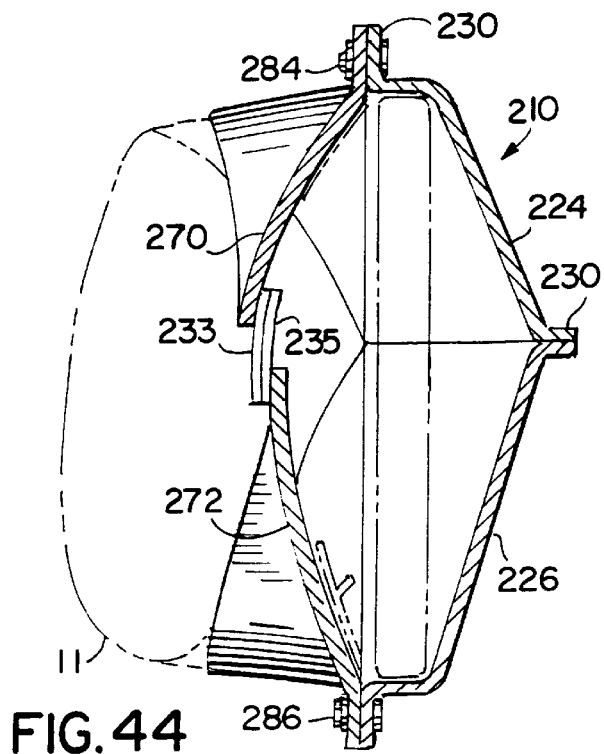
FIG. 44 is a sectional view of the case along line 44—44 of FIG. 42, showing the configuration of the case when being used to store a mask.

Referring now to FIG. 44, which is a cross sectional view of case 210 covering mask 11, the manner of holding case 210 upon mask 11 and the relationship of parts of case 210 may be understood. Closure panels 233, 235 may be used to secure mask 11 at least partially within case 210 while mask 11 is in storage within case 210.

While the foregoing embodiments have been described by way of example, it should be noted that additional modifications may be envisioned by those skilled in the art without departing from the spirit and scope of the appended claims. For example, various closure means may be provided for joining upper and lower rear panels 26 and 28, including devices such as snaps, zippers, buttons, and the like. In addition, while gusset members 42 and 44 have been described as being preferably lighter-weight synthetic fabrics or netting, other elements of case 10 may comprise such materials. Similarly, multi-layered materials may be used for some or all of the panels comprising case 10 where desired. This is particularly true where some or all of the panels of case 10 are used to support advertising indicia or logos (not shown in the figures). It is particularly anticipated that certain surfaces of case 10 may provide an excellent platform for such advertising indicia, such as rear panels 26 and 28 or front panel 24. It should also be noted that such indicia may be provided on either inner surfaces of these panels or outer surfaces, or both due to the fact that both inside and outside surfaces of these panels are visible in case 10 due to its inversion as it is converted between its folded, in-use configuration and its storage configuration. Moreover, in the embodiments described above having hook and loop fastening means on straps secured to the pouch, a portion of the hook material may be secured to part or all of rear panel 26, providing enhanced adjustability of the straps, particularly for small users. Finally, it should be noted that the opening (and closure means) of case 10 may be provided in various positions in addition to those described above. For example, a slot-type opening may be formed and disposed to fit against the user's head when in the worn position. Similarly, the opening described above along the lower edge of the case may be configured along an upper edge of the case. The openings described above, and shown in the Figures, as being disposed horizontally at or near the horizontal front centerline of the case and at a juncture of an upper front panel and a lower front panel may be instead disposed vertically, preferably but not necessarily at or near a vertical front centerline of the case, and at a juncture of a left front panel and a right front panel. The case may, but need not, be inverted (i.e., turned substantially inside out) to cover or contain a mask upon conversion of the case from a head band.

What is claimed is:

1. A convertible case and a mask combination, the case and mask combination comprising:
   a mask including a frame configured to fit sealingly around a portion of a user's face, at least one lens supported in the frame;
   a case including a flexible front panel and a flexible rear panel secured to the front panel, the rear panel defining with the front panel a pouch, the pouch having an opening through which the mask may be inserted into and removed from the pouch; and
   a first strap being attached to a first side region of the pouch and extending from the pouch toward the mask and attached to a first side of the mask, a second strap being attached to a second side region of the pouch opposite from the first side region and extending from the pouch toward the mask and attached to a second side of the mask;
   wherein the case is collapsible into a first, work configuration wherein the case bears against he user's head and a second, storage configuration wherein the mask is stored within the pouch such that the at least one lens is covered by the cover, the first and second straps being attached to the first and second sides of the mask and case respectively and being substantially clear of a region intermediate the first and second sides of the mask when the mask is in the storage configuration.

2. The case and mask of claim 1, wherein the front panel bears against the user's head in the first, worn configuration.

3. The case and mask of claim 2, wherein the rear panel includes an upper rear panel section and a lower rear panel section, and wherein the opening is defined between the upper and lower rear panel sections.

4. The case and mask of claim 3, wherein the mask and case each include a top portion and a bottom portion, the top portions of the mask and case being above the bottom portions of the mask and case when the mask and case are in the first worn configuration on a user's head, the top portion of the mask being proximate the top portion of the case when the mask is located within the pouch in the second stored configuration.

5. The case and mask of claim 2, wherein the front panel includes an upper front panel section and a lower front panel section, and wherein the opening is defined between the upper and lower rear panel sections.

6. The case and mask of claim 5, further comprising a first closure element secured adjacent to a lower edge of the upper panel section and a second closure element secured adjacent to an upper edge of the lower panel section, the first and second closure elements mutually cooperating to maintain the opening closed.

7. The case and mask of claim 5, wherein the mask and case each include a top portion and a bottom portion, the top portions of the mask and case being above the bottom portions of the mask and case when the mask and case are in the first worn configuration on a user's head, the top portion of the mask being proximate the bottom portion of the case when the mask is located within the pouch in the second stored configuration.

8. The case and mask of claim 2, wherein one of the front and rear panels includes a left panel section and a right panel section, and wherein the opening is vertical and is defined between the right and left panel sections.

9. The case and mask of claim 1, wherein the opening in the pouch is defined by an edge of the front panel and an edge of the rear panel.

10. The case and mask of claim 9 further comprising a central gusset, the gusset being attached to the front panel and to the rear panel, the gusset being foldable into a collapsed position between the front and rear panels.

11. A convertible case and a mask combination, the case and mask combination comprising:

a mask including a frame configured to fit securely around a portion of a user's face, at least on lens supported in the frame, the frame having a right side and a left side, the mask including a right and a left strap attachment structure being disposed on the right and left sides of the frame respectively; and a case including a flexible first panel and a flexible second panel secured to the first panel, the second panel defining with the first panel a convertible pouch, the pouch having an opening through which the mask may be inserted into and removed from the pouch, the pouch having a right and left side; and a strap system, the strap system including right and left strap portions configured for attachment to the right and left side of the pouch and to the right and left strap attachment structures respectively, the right and left strap portions extending between the pouch and the right and left attachment structures when the mask and pouch are worn around the user's head;

wherein the pouch is collapsible into a first, worn configuration witherein the pouch fits securely against the user's head, the left and right sides of the frame, and the left and right sides of the pouch being proximate the left and right sides of the user respectively, and a second, storage configuration wherein, the left and right sides of the mask fit within the left and right sides of the pouch respectively;

wherein the right and left strap portions are substantially clear of a region intermediate the right and left sides of the mask when the mask is in the storage configuration.

12. The case and mask of claim 11, wherein the mask and case each include a top portion and a bottom portion, the top portions of the mask and case being above the bottom portions of the mask and case when the mask and case are in the first worn configuration on a user's head, the top portion of the mask being proximate the top portion of the case when the mask is located within the pouch in the second stored configuration.

13. The case and mask of claim 11, wherein the mask and case each include a top portion and a bottom portion, the top portions of the mask and case being above the bottom portions of the mask and case when the mask and case are in the first worn configuration on a user's head, the top portion of the mask being proximate the bottom portion of the case when the mask is located within the pouch in the second stored configuration.

14. A mask and case combination comprising:

a mask including a front lens having an outward surface, the mask having a right and left side;

a case including a first flexible panel and a second flexible panel, the first and second panels defining a pouch therebetween, the pouch having an opening to receive the mask, the case having a right and left side;

a first strap extending between and connecting the right side of the case and the right side of the mask, and a second strap extending between and connecting the left side of the case and the left side of the mask;

the mask being in a first, worn configuration wherein the case bears against the user's head to secure the mask to the user's face, the left and right sides of the mask and the left and right sides of the case being proximate the left and right sides of the user respectively in the first worn configuration; and the mask being in a second, storage configuration wherein, the mask and case are rotated relative to each other, such that the left and right sides of the mask fit within the left and right sides of the pouch respectively, and the outward surface of the front lens being adjacent a portion of the case distal the opening.

15. The combination of claim 14 wherein the first flexible panel bears against the user's head in the first, worn configuration, the opening being in the first panel.

16. The combination of claim 15 wherein the first panel and the second panel each include an external facing surface and an internal facing surface, the outward surface of the front lens being adjacent to the internal facing surface of the first panel.

17. The combination of claim 16 wherein the first and second straps are attached to the first and second sides of the mask and case respectively and being substantially clear of a region intermediate the left and right sides of the mask when the mask is in the storage configuration.

18. The combination of claim 17 wherein, the left and right portions of the mask fit within the left and right sides of the pouch respectively in the storage configuration.

19. The combination of claim 14 wherein the first flexible panel bears against the user's head in the first, worn configuration, the opening being in the second panel.

* * * * *